United States Patent
Motion et al.

(10) Patent No.: US 11,707,612 B2
(45) Date of Patent: Jul. 25, 2023

(54) INTELLIGENT BIOELECTRIC MODULE FOR USE WITH DRUG DELIVERY SYSTEM

(71) Applicant: Bioelectric Devices, Inc., Menlo Park, CA (US)

(72) Inventors: Michael Motion, San Jose, CA (US); Michel M. Maharbiz, El Cerrito, CA (US); Russell Potts, San Francisco, CA (US)

(73) Assignee: Bioelectric Devices, Inc., Menlo Park, CA (US)

( * ) Notice: Subject to any disclaimer, the term of this patent is extended or adjusted under 35 U.S.C. 154(b) by 467 days.

(21) Appl. No.: 17/034,474

(22) Filed: Sep. 28, 2020

(65) Prior Publication Data

US 2021/0023353 A1 Jan. 28, 2021

Related U.S. Application Data

(62) Division of application No. 15/661,813, filed on Jul. 27, 2017, now Pat. No. 10,842,979.

(60) Provisional application No. 62/399,284, filed on Sep. 23, 2016, provisional application No. 62/367,711, filed on Jul. 28, 2016.

(51) Int. Cl.
*A61N 1/30* (2006.01)
*A61M 35/00* (2006.01)

(52) U.S. Cl.
CPC ..... *A61M 35/00* (2013.01); *A61M 2205/3303* (2013.01); *A61M 2205/3317* (2013.01); *A61M 2205/3584* (2013.01); *A61M 2205/52* (2013.01); *A61M 2205/6072* (2013.01); *A61M 2230/04* (2013.01)

(58) Field of Classification Search
CPC .......... A61N 1/327; A61N 1/30; A61B 18/14; A61M 2205/3317; A61M 2205/3303; A61M 2205/52; A61M 35/00; A61M 37/00
See application file for complete search history.

(56) References Cited

U.S. PATENT DOCUMENTS

| | | | |
|---|---|---|---|
| 6,009,344 | A | 12/1999 | Flower et al. |
| 6,144,869 | A | 11/2000 | Berner et al. |
| 6,377,848 | B1 | 4/2002 | Garde et al. |
| 6,391,015 | B1 | 5/2002 | Millot |
| 6,424,862 | B1 | 7/2002 | Brown, III et al. |
| 6,738,662 | B1 | 5/2004 | Frank |
| 7,869,855 | B2 | 1/2011 | Meyer et al. |
| 8,214,031 | B1 | 7/2012 | Sexton |
| 10,512,431 | B2 | 12/2019 | Cheng |
| 2002/0183683 | A1 | 12/2002 | Lerner |
| 2002/0183685 | A1 | 12/2002 | Crawford et al. |

(Continued)

*Primary Examiner* — Rebecca E Eisenberg
(74) *Attorney, Agent, or Firm* — Sunstein LLP

(57) ABSTRACT

An intelligent bioelectric module for use with a drug delivery system has a case and a set of at least two electrodes in electrical communication with a detection surface of the case. The case is configured so that, in use, the detection surface comes into electrical communication with (i) a second surface of the delivery system when a first surface of the delivery system has been put into contact with a tissue surface of a human or animal subject or (ii) the tissue surface that is adjacent to a portion contacted by the first surface of the delivery system or (iii) both the second surface and the tissue surface.

4 Claims, 16 Drawing Sheets

(56) References Cited

U.S. PATENT DOCUMENTS

| | | |
|---|---|---|
| 2005/0107832 A1* | 5/2005 | Bernabei ................ A61N 1/327 607/3 |
| 2008/0220092 A1 | 9/2008 | Dipierro et al. |
| 2009/0299266 A1 | 12/2009 | Bernabei |
| 2010/0137780 A1 | 6/2010 | Singh et al. |
| 2010/0149042 A1 | 6/2010 | Utsi et al. |
| 2010/0204637 A1 | 8/2010 | Imran |
| 2011/0015625 A1 | 1/2011 | Adanny et al. |
| 2012/0150098 A1 | 6/2012 | Etheredge et al. |
| 2013/0345620 A1 | 12/2013 | Zemel et al. |
| 2014/0148887 A1 | 5/2014 | Grob et al. |
| 2015/0374984 A1 | 12/2015 | King et al. |
| 2016/0128589 A1 | 5/2016 | Tabib-Azar |
| 2017/0232249 A1 | 8/2017 | Pinna |
| 2018/0326201 A1 | 11/2018 | Nagel et al. |
| 2019/0247234 A1 | 8/2019 | Prakash et al. |
| 2019/0275320 A1 | 9/2019 | Kim et al. |
| 2019/0388667 A1 | 12/2019 | Xu |

\* cited by examiner

BREAKTHROUGH FEATURES

✻ PatchTrack™
Autoatically recognizes when patient is wearing patch

⌘ Product Monitoring
Monitor if patch was altered in any way.

❀ Patient Support
Compliance monitoring, medication adherence, physiological monitoring and behavioral support ✸ Physiological Hub
Hub can be expanded to include: Heart Rate, Galvanic Skin Response, Temperature, EKG, EMG

ESSENTIALS

★ Compact Design
1" diameter and 2mm height

✢ TD Compatibility
Compatible with most transdermal products

★ Cloud Syncing
Sync data and vitals wirelessly to mobile phones, watches, tablets ◉ Body Area Networks
Integrate with other wearable devices that collect health data

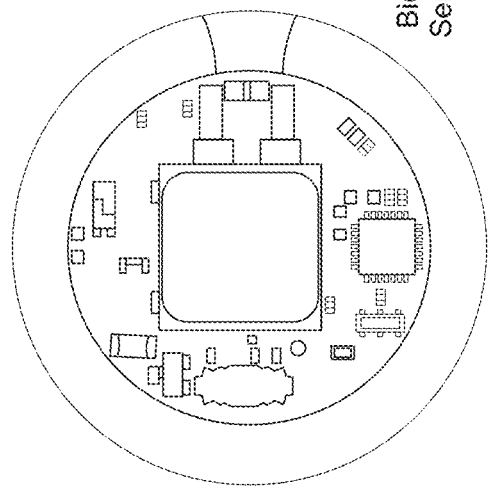

Bioelectric Sensor Hub

*Fig. 5A*

INTELLIGENT BIOELECTRIC MODULE FOR USE WITH DRUG DELIVERY SYSTEM

RELATED APPLICATIONS

This application is a divisional of U.S. application Ser. No. 15/661,813 filed Jul. 27, 2017, which claims the benefit of U.S. provisional application Ser. No. 62/367,711 filed Jul. 28, 2016, and of U.S. provisional application Ser. No. 62/399,284 filed Sep. 23, 2016. Each of these related applications is hereby incorporated herein by reference in its entirety.

TECHNICAL FIELD

The present invention relates to bioelectrical modules for use with drug delivery systems, and more particularly to combinations of such modules and systems that are wearable.

SUMMARY OF EMBODIMENTS

In one embodiment, the present invention provides an intelligent bioelectric module for use with a drug delivery system. In this embodiment, the module includes:
a case;
a set of at least two electrodes in electrical communication with a detection surface of the case;
wherein the case is configured so that, in use, the detection surface comes into electrical communication with (i) a second surface of the delivery system when a first surface of the delivery system has been put into contact with a tissue surface of a human or animal subject or (ii) the tissue surface that is adjacent to a portion contacted by the first surface of the delivery system or (iii) both the second surface and the tissue surface; and
electronics disposed within the case that determines if a quantity related to electrical impedance, over a path that includes the set of electrodes and material in the second surface or the tissue surface or material in both the second surface and the tissue surface, is within a predetermined limit, wherein, if so, the bioelectric module has been determined to be operatively coupled to the drug delivery system.

In another embodiment, the present invention provides an intelligent bioelectric module for use with a drug delivery system. The module of this embodiment includes:
a case;
a set of at least two electrodes in electrical communication with a detection surface of the case;
wherein the case is configured so that, in use, the detection surface comes into electrical communication with (i) a second surface of the delivery system when a first surface of the delivery system has been put into contact with a tissue surface of a human or animal subject or (ii) the tissue surface that is adjacent to a portion contacted by the first surface of the delivery system or (iii) both the second surface and the tissue surface; and
electronics disposed within the case that determines if a quantity related to an RC time constant, with the resistance R and capacitance C experienced over a path that includes the set of electrodes and material in the second surface or the tissue surface or material in both the second surface and the tissue surface, is within a predetermined limit; wherein, if so, the drug delivery system has been determined to be operatively coupled to the tissue.

In yet another embodiment, the invention provides an intelligent bioelectric module for use with a drug delivery system. In this embodiment, the module includes:
a case;
a set of at least two electrodes in electrical communication with a detection surface of the case;
wherein the case is configured so that, in use, the detection surface comes into electrical communication with (i) a second surface of the delivery system when a first surface of the delivery system has been put into contact with a tissue surface of a human or animal subject or (ii) the tissue surface that is adjacent to a portion contacted by the first surface of the delivery system or (iii) both the second surface and the tissue surface; and
electronics disposed within the case that determines if a quantity related to impedance to an AC signal, over a path that includes the set of electrodes and material in the second surface or the tissue surface or material in both the second surface and the tissue surface, is within a predetermined limit; wherein, if so, the drug delivery system has been determined to be coupled to tissue as opposed to non-living material.

In a related embodiment, the electronics repeatedly determines if the quantity is within the predetermined limit, so as to determine over time if the drug delivery system is operatively coupled to the tissue.

Alternatively or in addition, the module further includes a layer of electrically conductive material disposed between the detection surface of the module and the second surface of the delivery system.

In another embodiment, the invention provides an intelligent bioelectric module for use with a drug delivery system. In this embodiment, the module includes:
a case;
a set of at least two electrodes in electrical communication with a detection surface of the case, wherein one or more dielectric materials are disposed between the detection surface and the electrodes;
wherein the case is configured so that, in use, the detection surface comes into electrical communication with (i) a second surface of the delivery system when a first surface of the delivery system has been put into contact with a tissue surface of a human or animal subject or (ii) the tissue surface that is adjacent to a portion contacted by the first surface of the delivery system or (iii) both the second surface and the tissue surface; and
electronics disposed within the case that determines if a quantity related to an RC time constant, with the resistance R and capacitance C experienced over a path that includes (i) the set of electrodes, (ii) the dielectric, and (iii) material in the second surface or the tissue surface or material in both the second surface and the tissue surface, is within a predetermined limit; wherein, if so, the coupling between the bioelectric module and the drug delivery system has been determined to be sufficient.

In a further related embodiment, the dielectrics have a known impedance and known shape and the geometrical area is equal or less than the detection surface of the case. Optionally, one or more dielectrics are placed underneath or adjacent to each electrode.

BRIEF DESCRIPTION OF THE DRAWINGS

The foregoing features of embodiments will be more readily understood by reference to the following detailed description, taken with reference to the accompanying drawings, in which:

FIG. 5A presents a bottom view and key features of an intelligent bioelectric module chip in accordance with an embodiment of the present invention;

DETAILED DESCRIPTION OF SPECIFIC EMBODIMENTS

Definitions

As used in this description and the accompanying claims, the following terms shall have the meanings indicated, unless the context otherwise requires:

A "drug delivery system" is a set components configured to deliver drug to a human or animal subject, through either passive or active delivery mechanisms.

A "bioelectric module" is a device that can be coupled to or integrated into a drug delivery system, for use with a human or animal subject, and that performs a function selected from the group consisting of controlling drug delivery from the drug delivery system, monitoring drug delivery from the drug delivery system, monitoring a set of physiological parameters of the human or animal subject, storing, processing and transmitting data, and combinations thereof.

"Tissue" means tissue of a human or animal subject.

A "set" includes at least one member.

A "case" of a bioelectric module is an outer layer of material having an exterior surface that protects components of the module that lie beneath the layer.

"Electrical communication" of a set of at least two electrodes with a given surface means physical proximity to the given surface, either by direct contact or through an electrically conductive material, that is sufficient to permit useful measurement of electrical impedance over a path that includes the set of electrodes and material in the given surface.

Figure 1A:
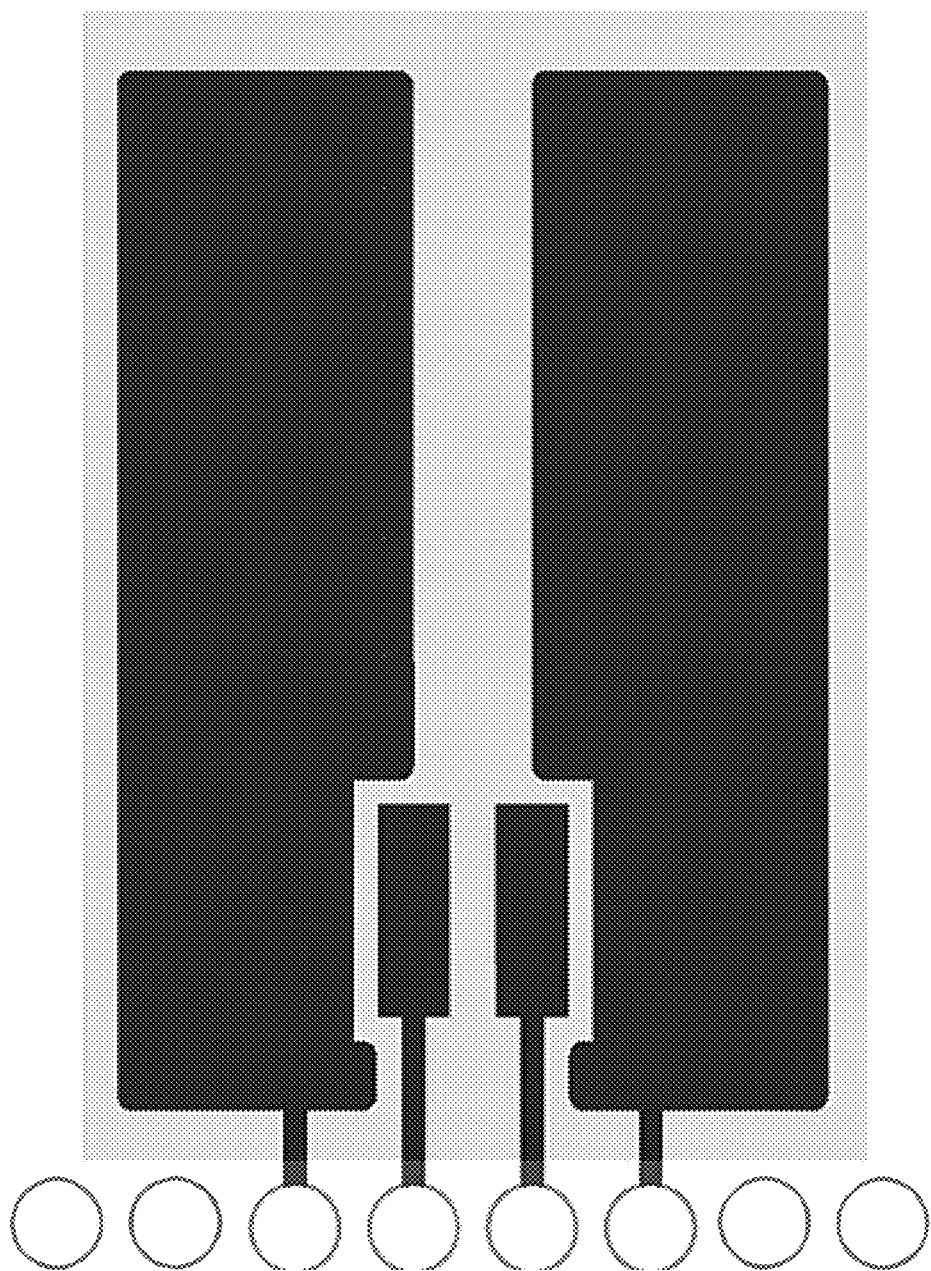
FIG. 1A is an electrode array including first and second electrode pairs used for sensing in accordance with an embodiment of the present invention.

FIG. 1A is an electrode array including first and second electrode pairs used for sensing in accordance with an embodiment of the present invention. The two smaller electrodes are the first pair of electrodes and they are used in the first measurement modality to determine contact or integration of the bioelectric module with a drug delivery system, in this case a patch. The two large electrodes are used in the second measurement modality to determine proximity of the drug delivery system to the skin.

Figure 1B:
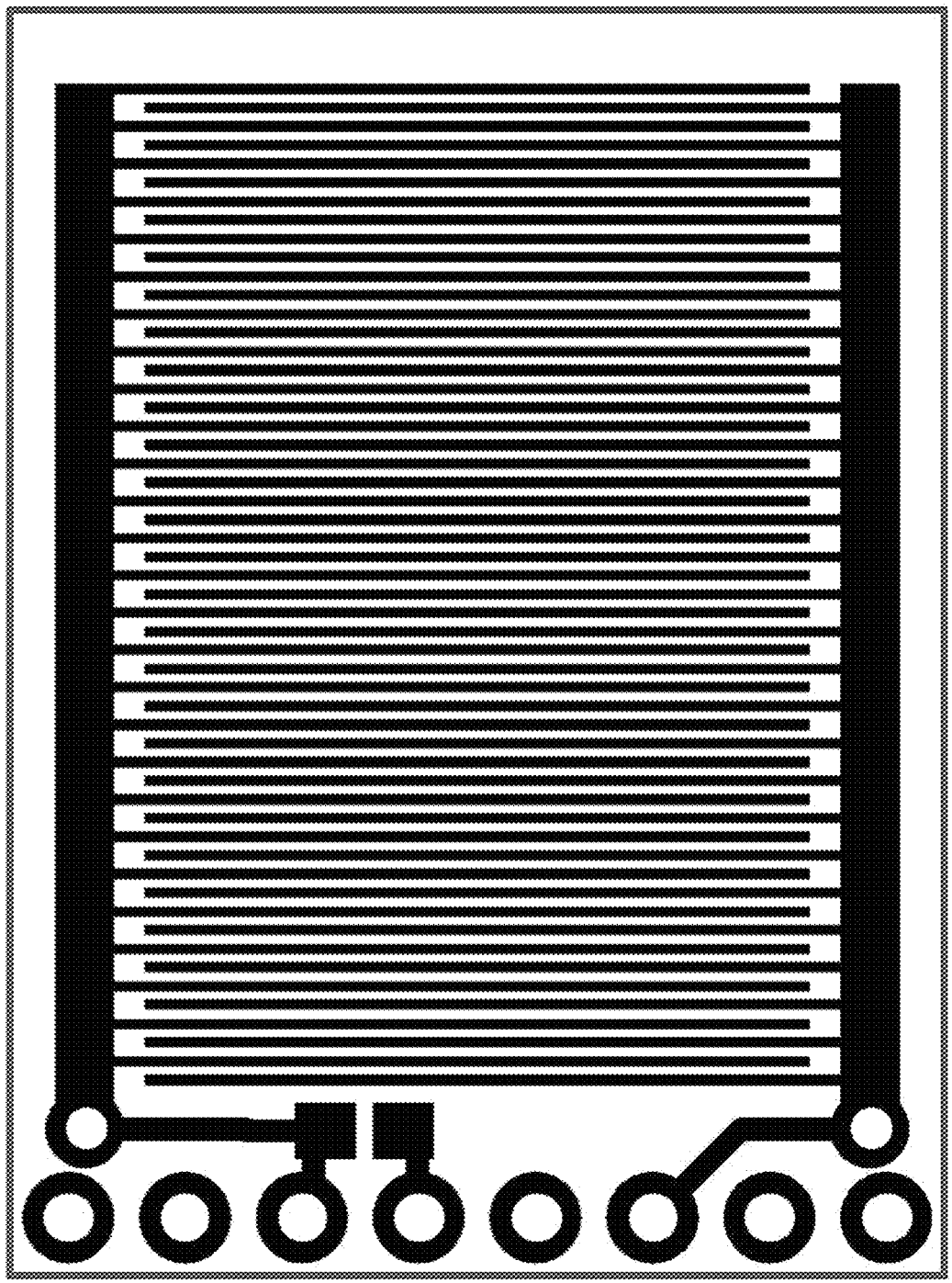
FIG. 1B is a multi-electrode array for detecting proximity to a biological tissue as well as patch contact in accordance with an embodiment of the present invention.

FIG. 1B is a multi-electrode array for detecting proximity to a biological tissue as well as patch contact in accordance with an embodiment of the present invention.

Figure 2A:
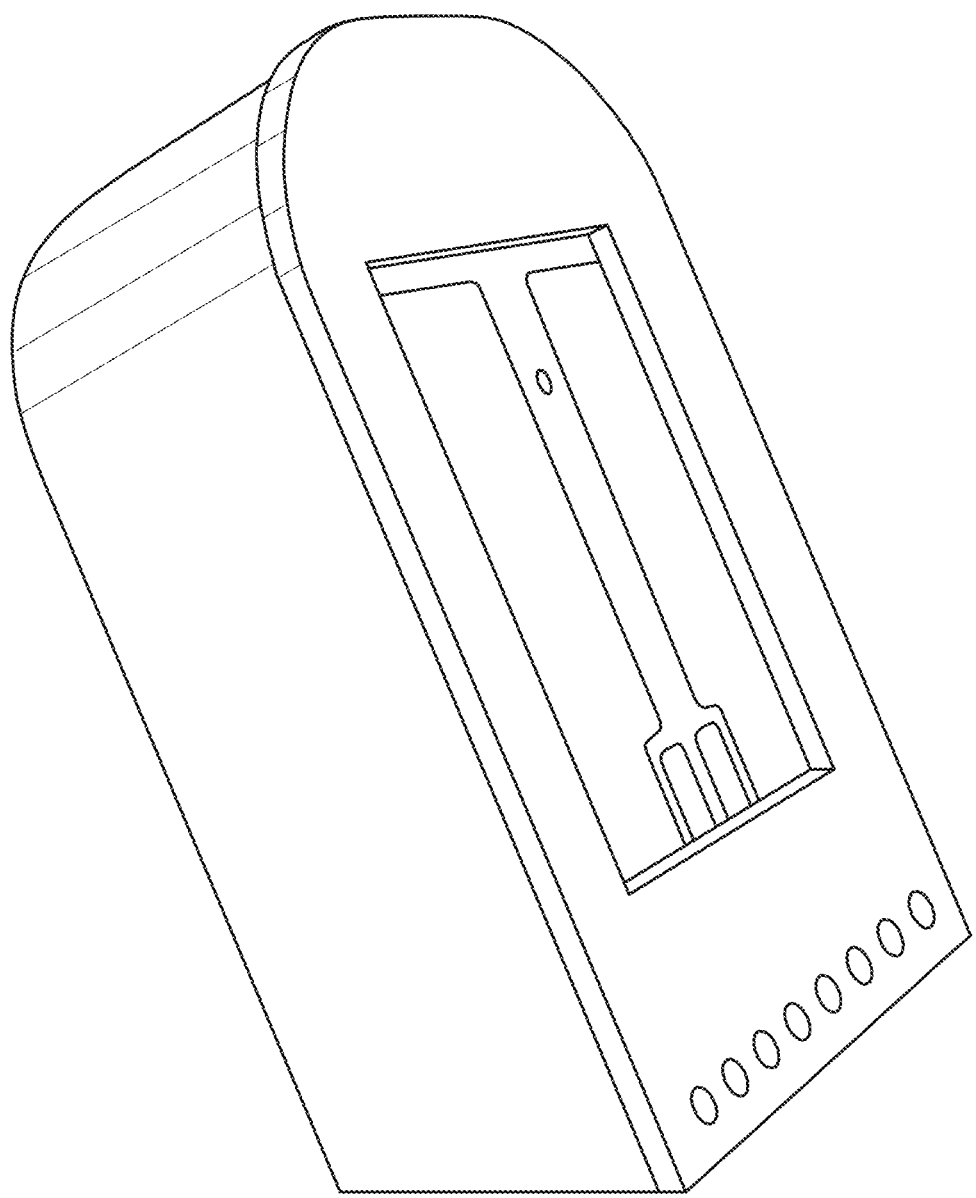
FIG. 2A is an intelligent bioelectric module equipped with the electrode array of FIG. 1A visible through a case, in this example a plastic enclosure, in accordance with an embodiment of the present invention.

FIG. 2A is an intelligent bioelectric module equipped with the electrode array of FIG. 1A visible through a case, in this example a plastic enclosure, in accordance with an embodiment of the present invention.

Figure 2B:
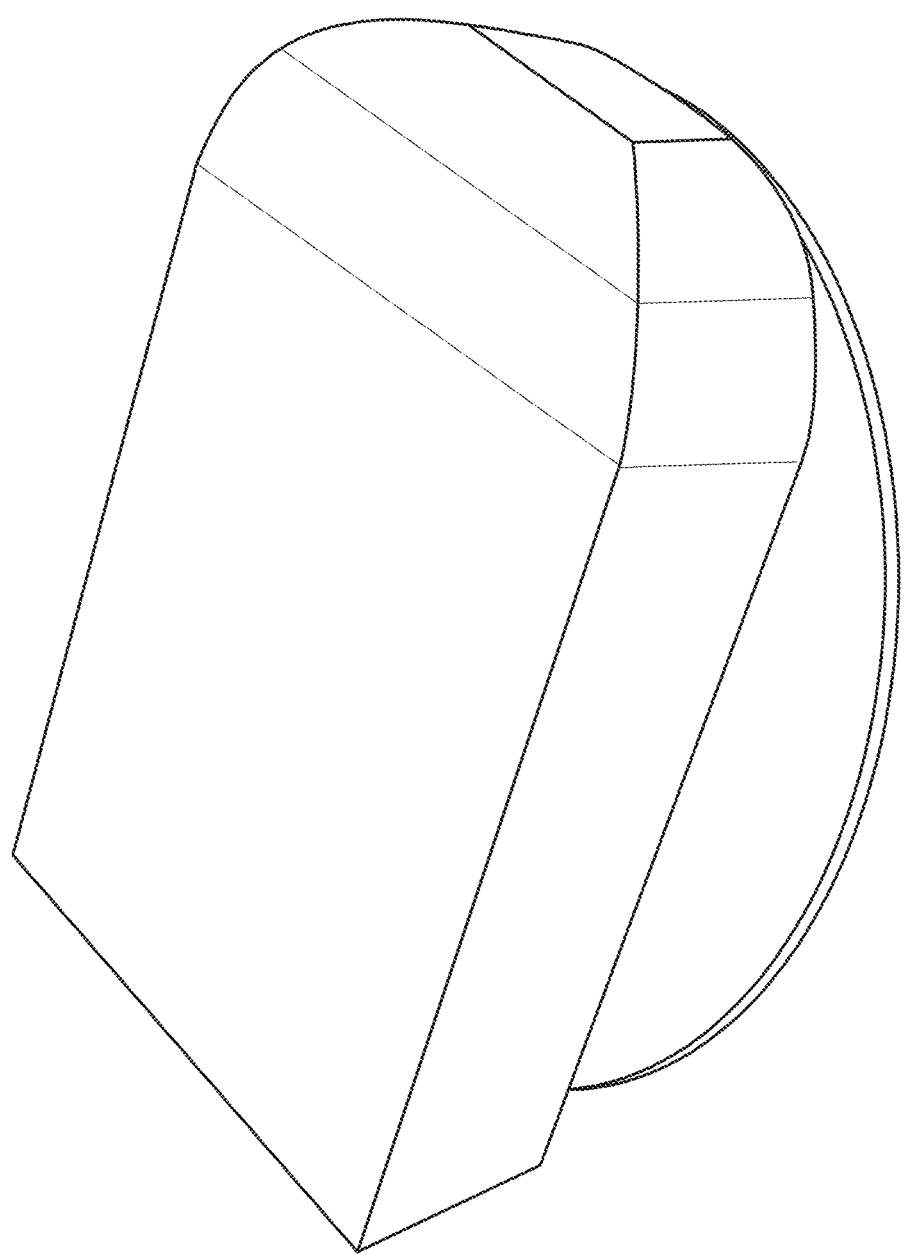
FIG. 2B shows the bioelectric module of FIG. 2A coupled to an underlying skin patch, in accordance with an embodiment of the present invention.
Figure 3A:
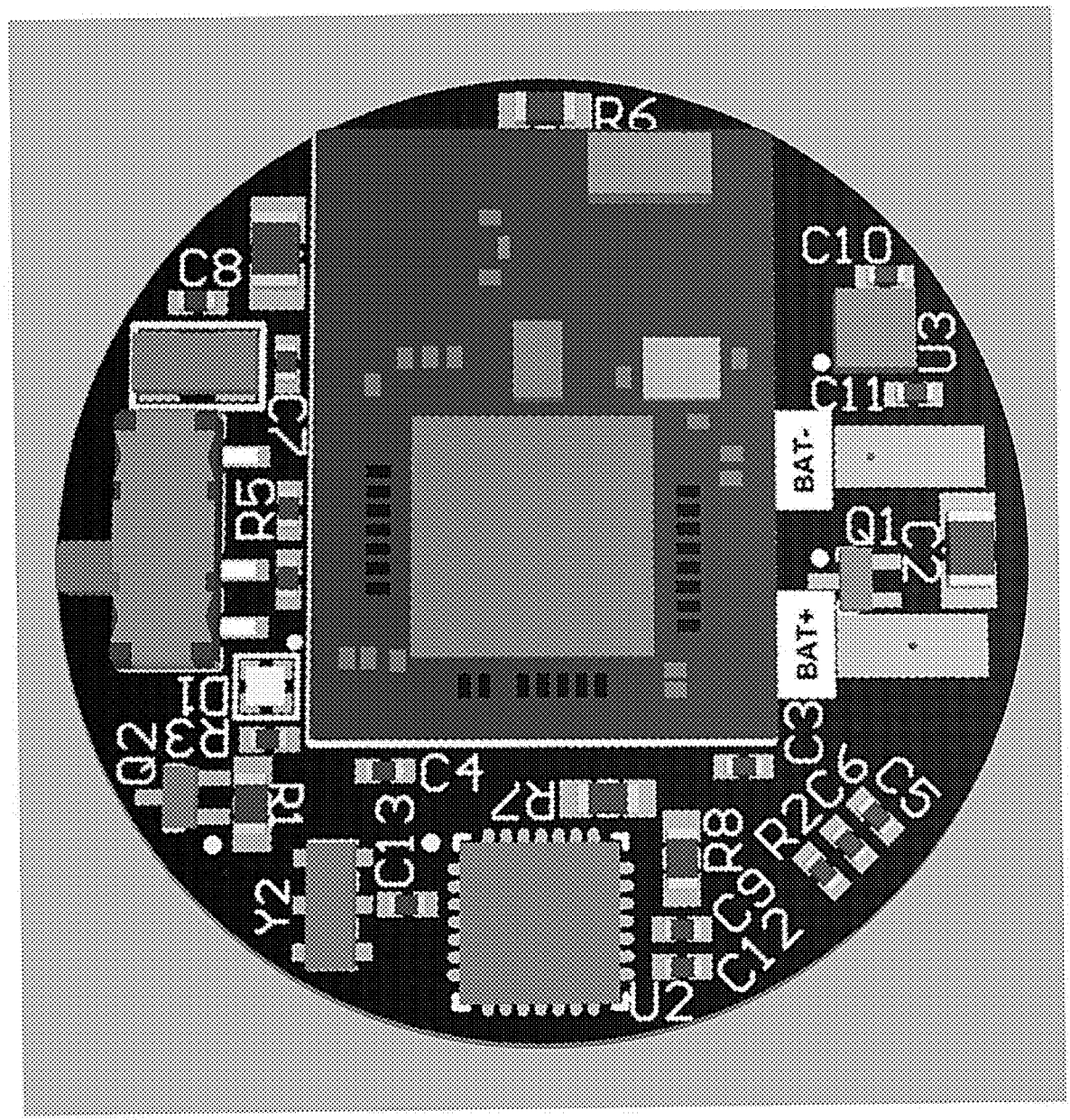
FIGS. 3A through 3F show successive views of an intelligent bioelectric module chip containing a microcontroller, memory module, power module, communication module, sensor modules, and additional modules to use with a wearable device or drug delivery system, in accordance with an embodiment of the present invention.
Figure 3B:
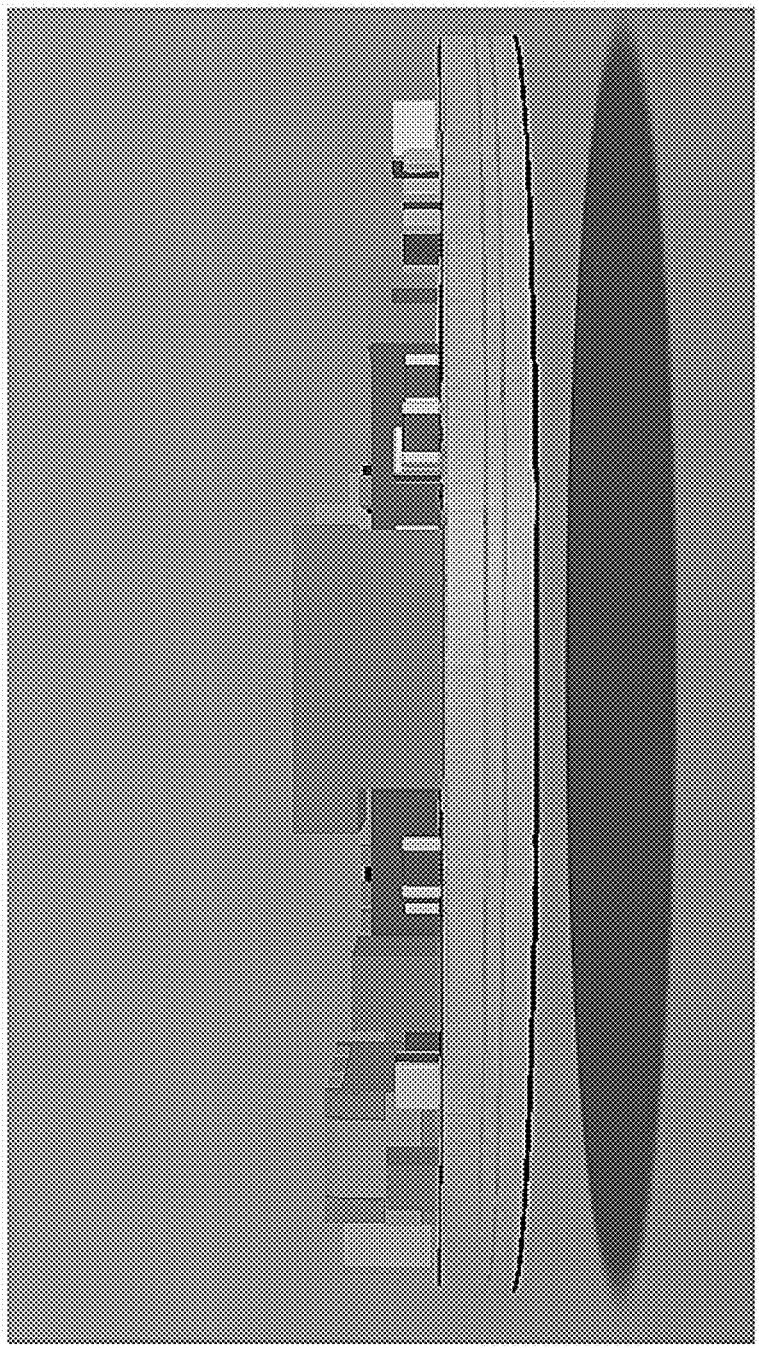
Figure 3C:
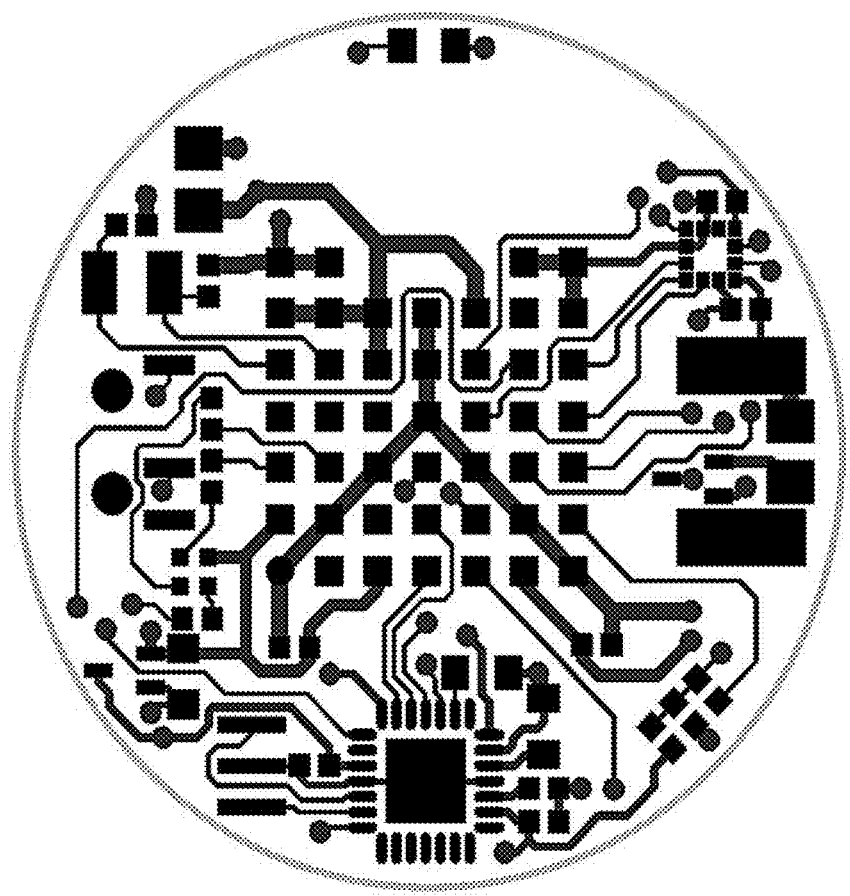
Figure 3D:
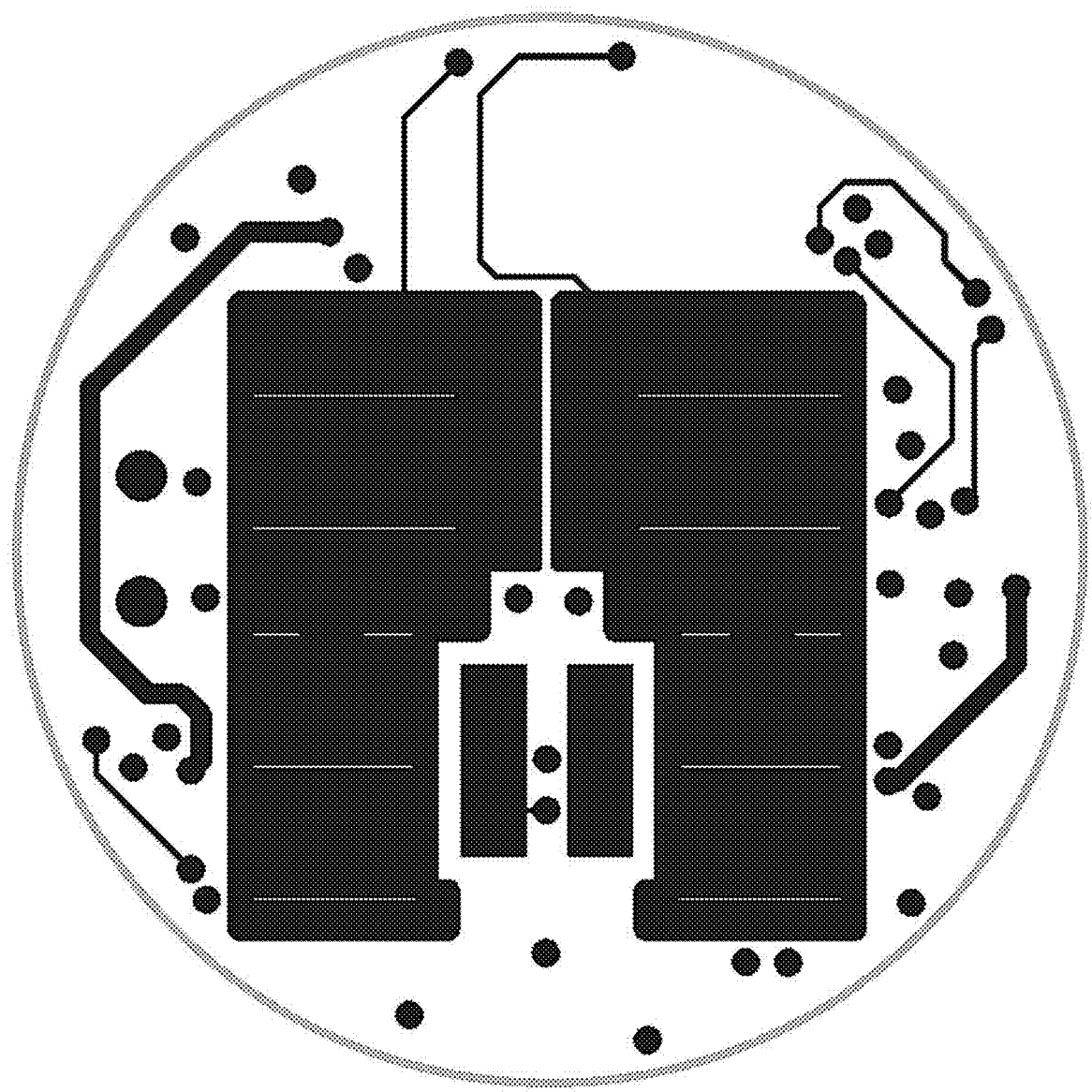
Figure 3E:
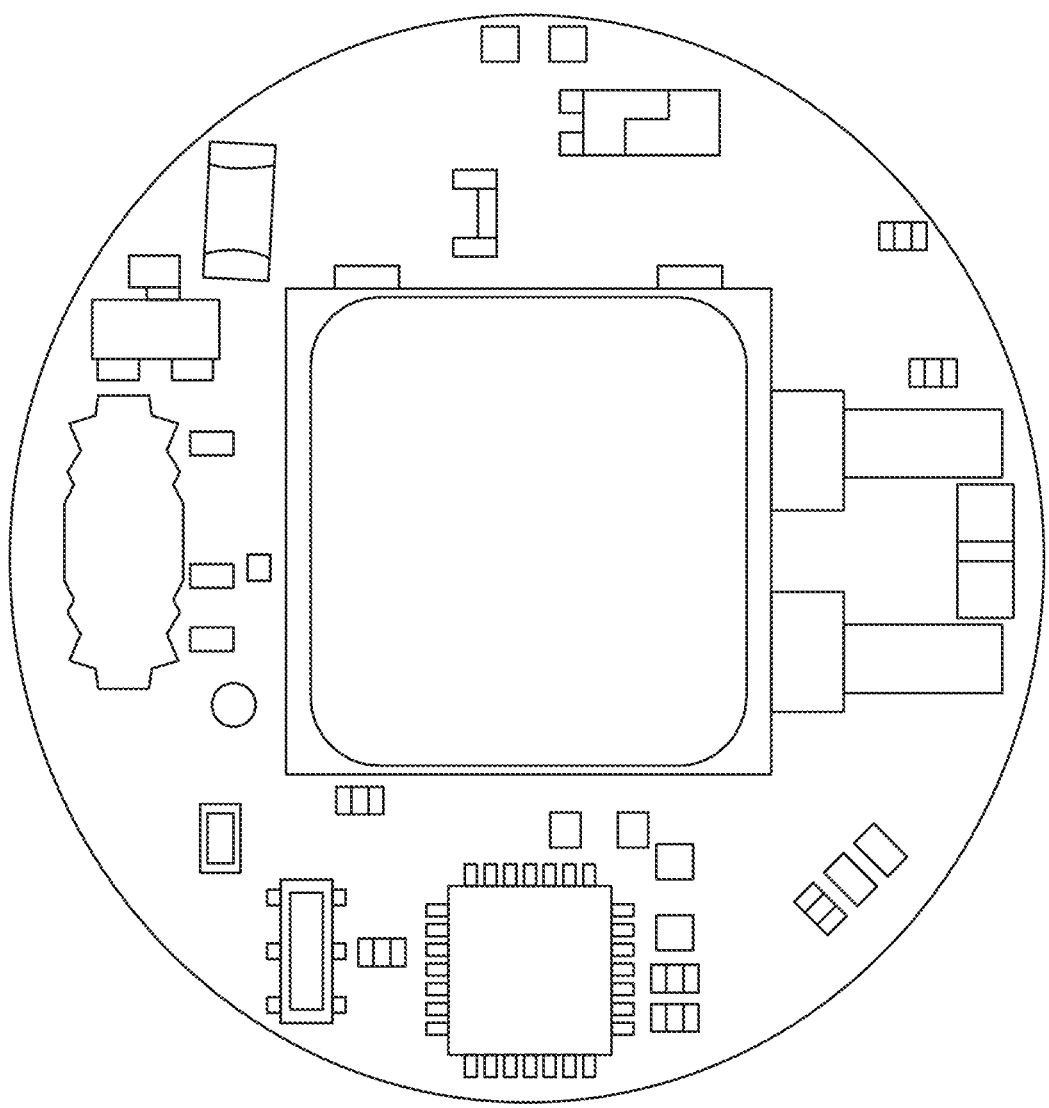
Figure 3F:
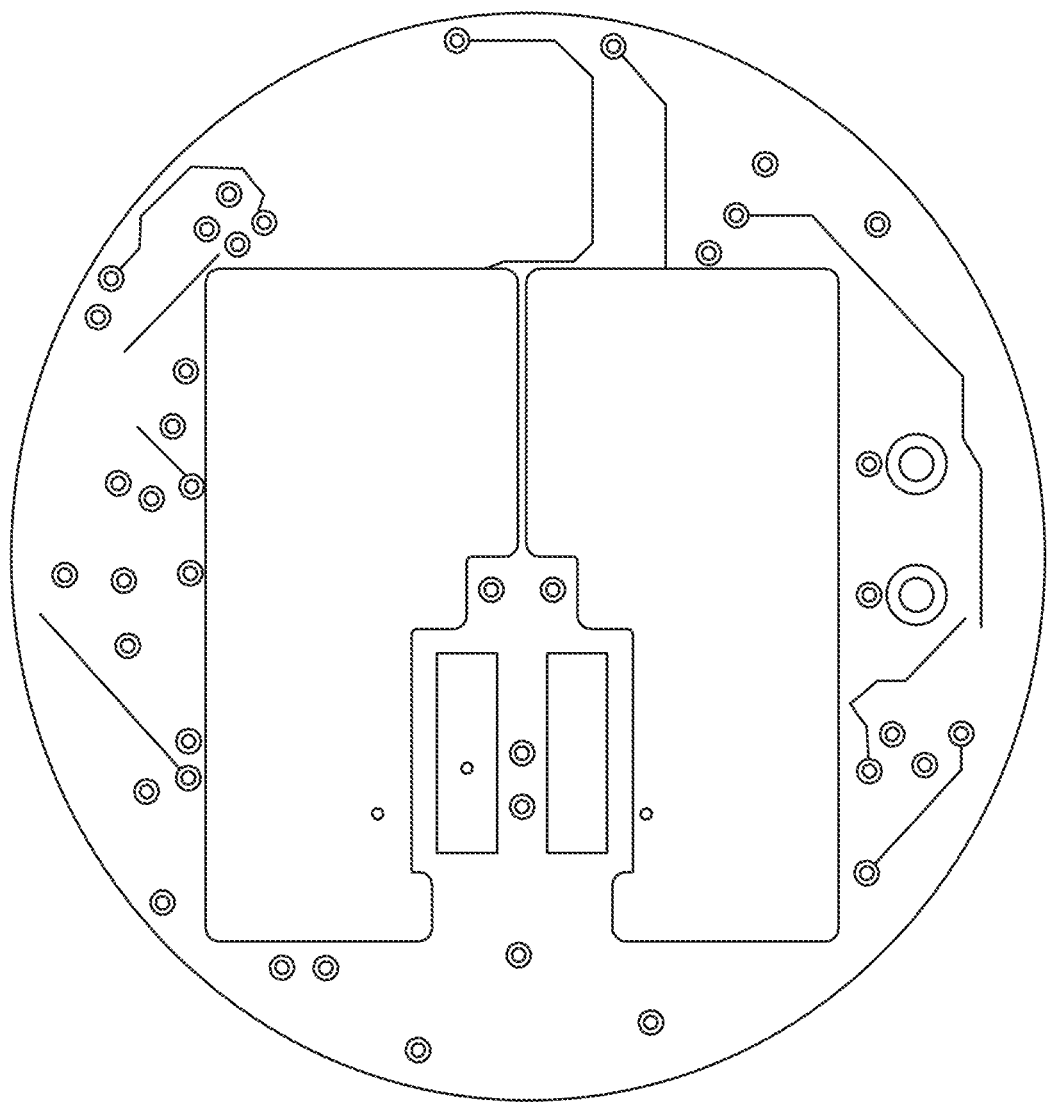

FIG. 2B shows the bioelectric module of FIG. 2A coupled to an underlying skin patch, in accordance with an embodiment of the present invention.

FIGS. 3A through 3F show successive views of an intelligent bioelectric module chip containing a microcontroller, memory module, power module, communication module, sensor modules, and additional modules to use with a wearable device or drug delivery system, in accordance with an embodiment of the present invention.

Figure 4:
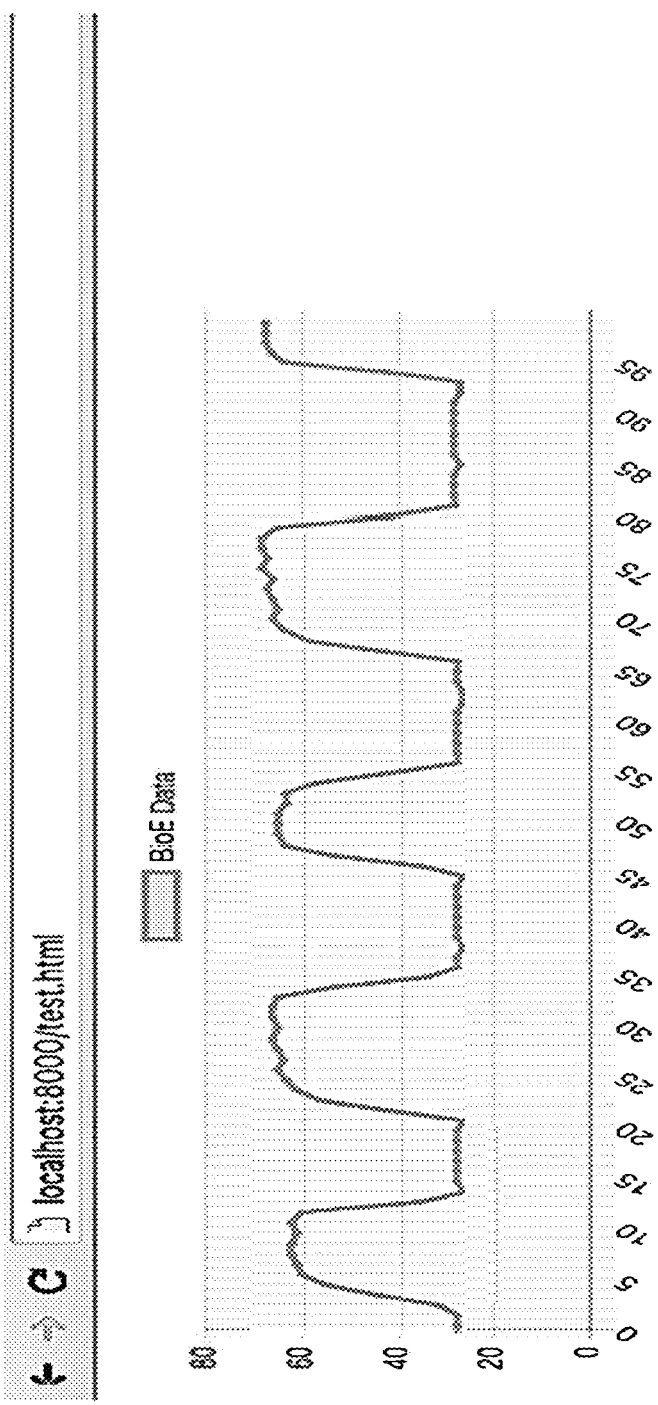
FIG. 4 is a graph showing representative proximity sensor data as measured and transmitted by an intelligent bioelectric device in accordance with an embodiment of the present invention, wherein signal strength is plotted in arbitrary units on the Y-axis against time in arbitrary units on the X-axis.

FIG. 4 is a graph showing representative proximity sensor data as measured and transmitted by an intelligent bioelectric device in accordance with an embodiment of the present invention;

FIG. 5A presents a bottom view and key features of an intelligent bioelectric module chip in accordance with an embodiment of the present invention.

Figure 5B:
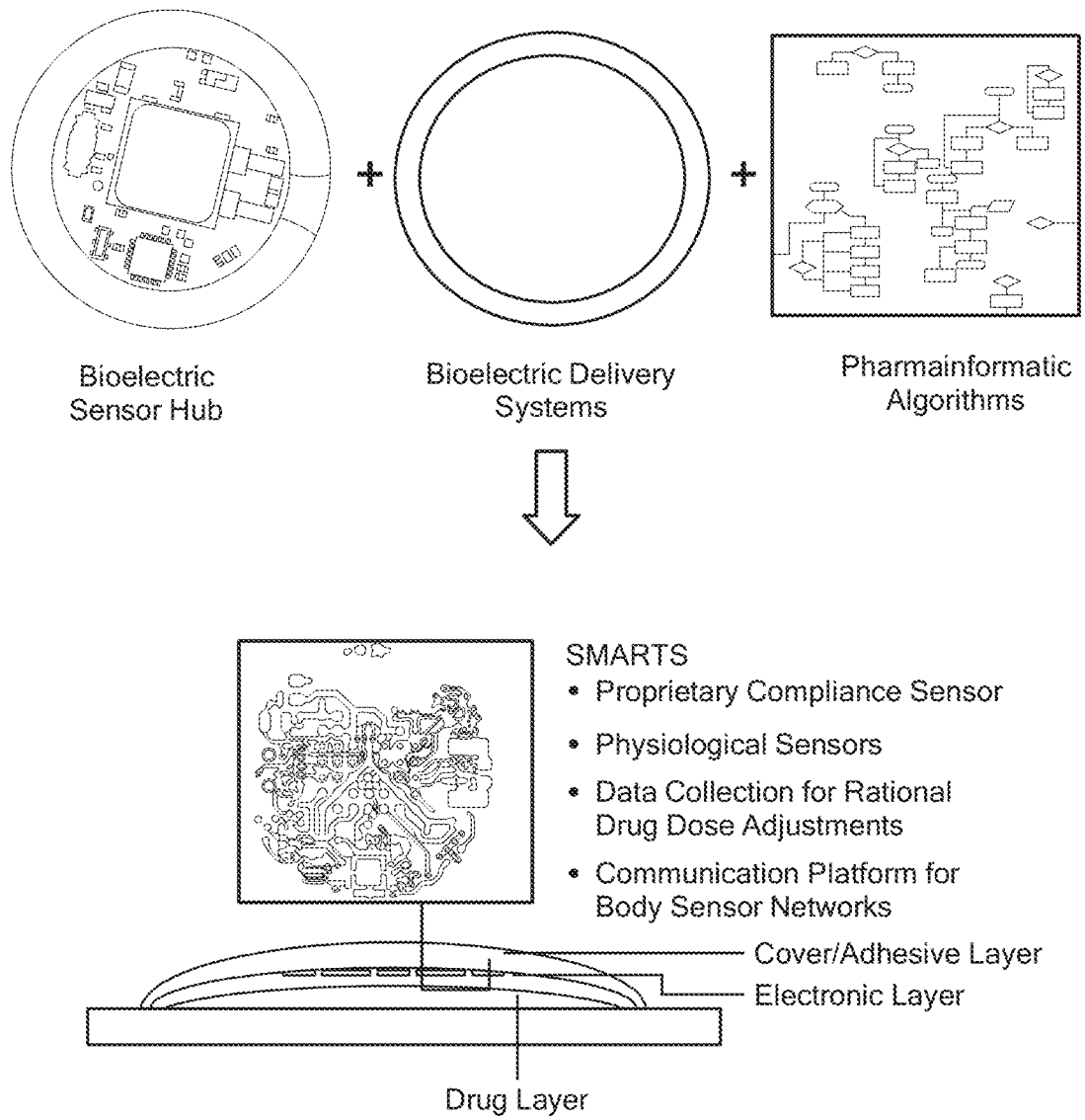
FIG. 5B presents a symbolic view of an embodiment of the present invention in which are provided a bioelectric module chip, a delivery system and a set of pharmacoinformatic algorithms.

FIG. 5B presents a symbolic view of an embodiment of the present invention in which are provided a bioelectric module chip, a delivery system and a set of pharmacoinformatic algorithms.

Figure 6:
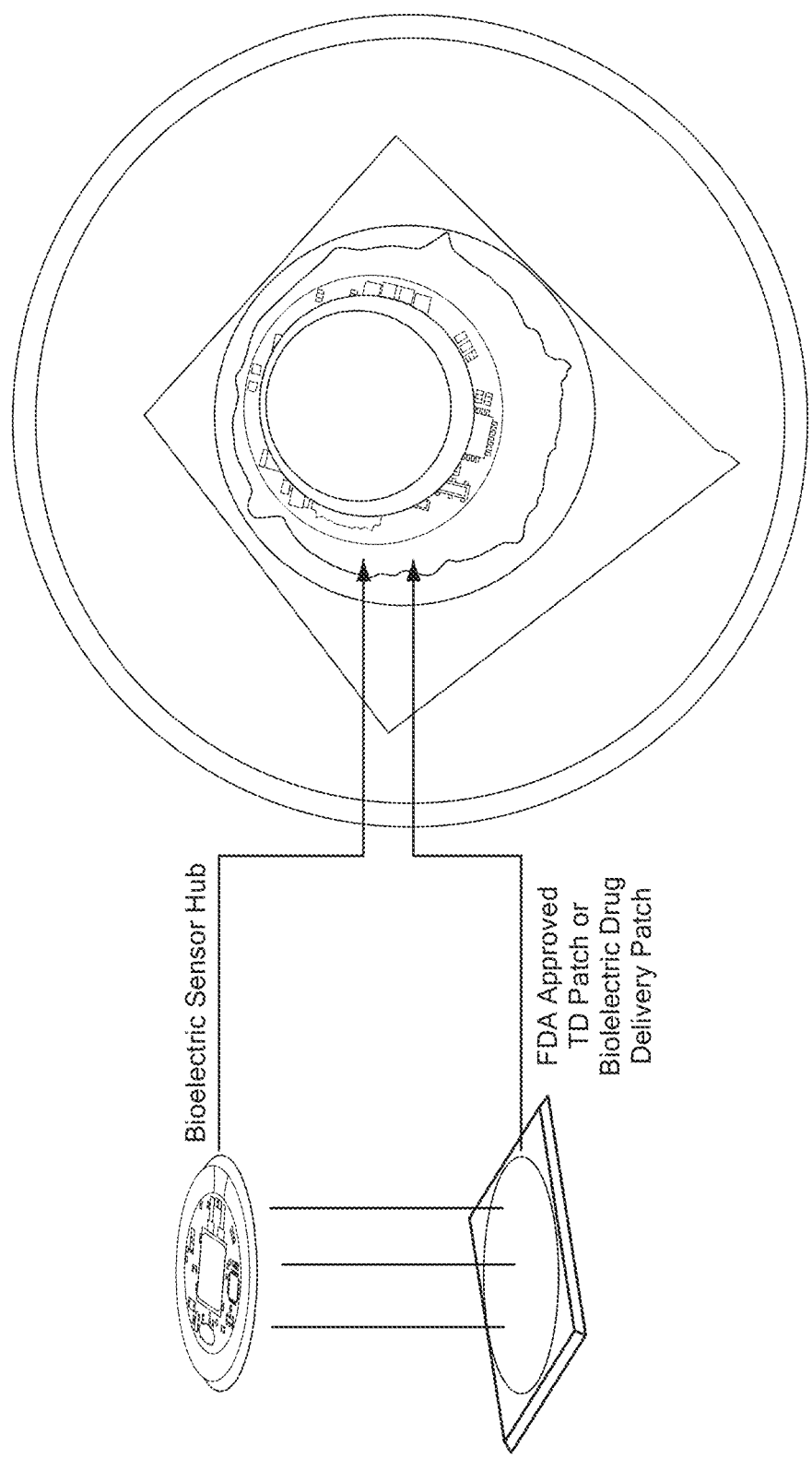
FIG. 6 is a view of an embodiment of the present invention in which a bioelectric module is coupled to a drug delivery system, in this case, a passive transdermal patch.

FIG. 6 is a view of an embodiment of the present invention in which a bioelectric module is coupled to a drug delivery system, in this case, a passive transdermal patch.

Figure 7:
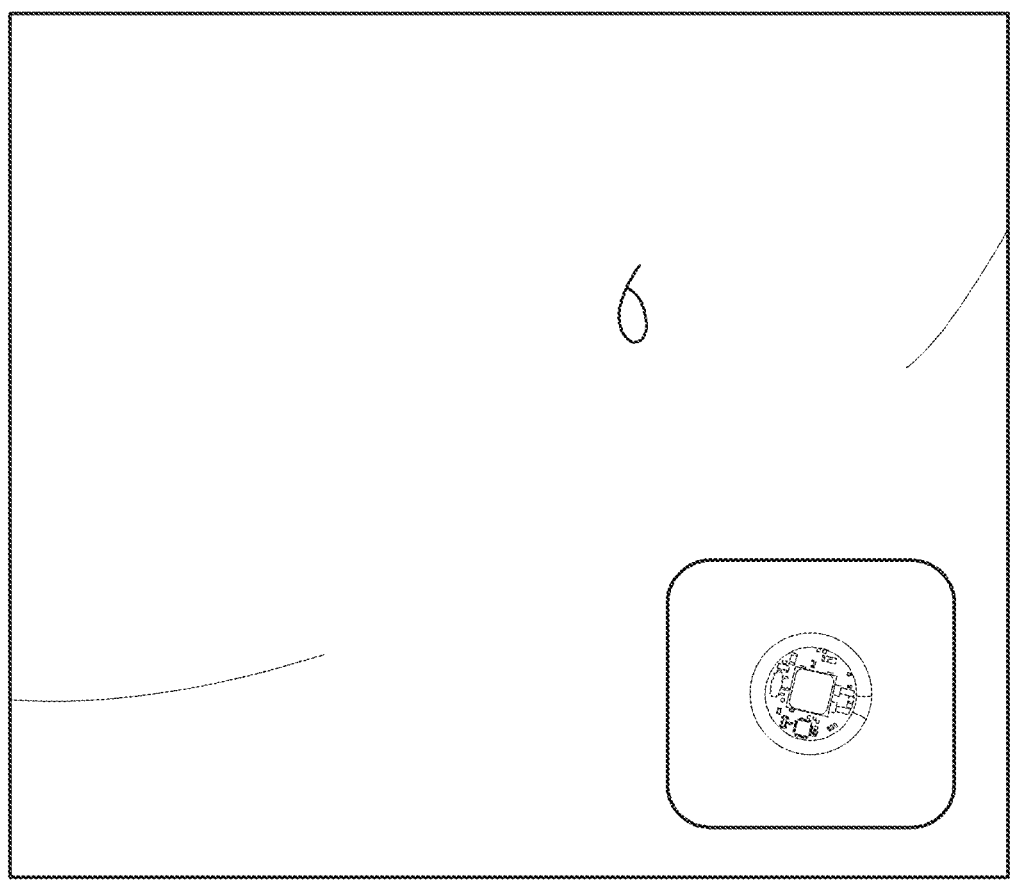
FIG. 7 illustrates the application of the embodiment of FIG. 6 to a human subject.

FIG. 7 illustrates the application of the embodiment of FIG. 6 to a human subject.

Figure 8:
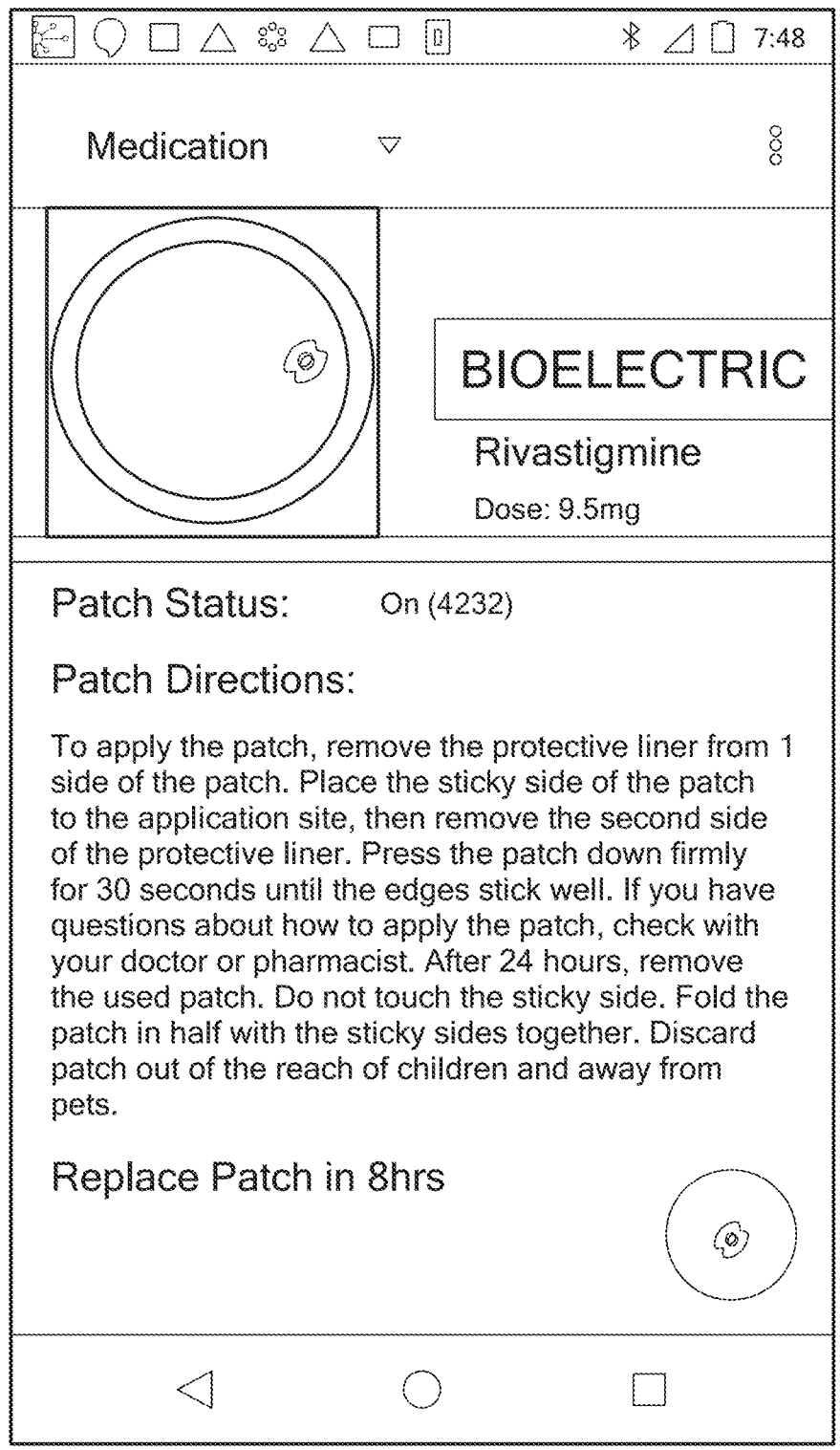
FIG. 8 is a representation of a display on a smart mobile phone, to which is coupled an intelligent bioelectric module via Bluetooth communication, wherein the mobile phone is executing an application by which information about operation of the module is presented in the display, in accordance with an embodiment of the present invention.

FIG. 8 is a representation of a display on a smart mobile phone, to which is coupled an intelligent bioelectric module via Bluetooth communication, wherein the mobile phone is executing an application by which information about operation of the module is presented in the display, in accordance with an embodiment of the present invention. The application searches for, connects with, and communicates with the bioelectric module and displays various types of information. More specifically, the system provides information relating to compliance with and adherence to a medication regimen.

In accordance with one embodiment of the invention, a battery-powered, wirelessly-communicating intelligent bioelectric module for use with a drug delivery system, in a first detection modality, detects when the module has been operatively coupled to a drug delivery system. Subsequently, in a second detection modality, the control module detects when the coupled drug delivery system has been brought into electrical communication with tissue, ensuring compliance of use. Subsequently, in a third detection modality, the bioelectric module verifies proper drug delivery proximity to a biological tissue by measuring and analyzing the underlying electrical properties of the tissue.

The first detection modality of this embodiment, that of proper configuration between the bioelectric module and the drug delivery system, is implemented via a set of at least two conducting electrodes placed in electrical communication with a surface (which we shall call the "detection surface") of the bioelectric module facing (in a first sub-embodiment) what we call the second surface of the drug delivery system, which may, for example, be a patch. The first surface of the drug delivery system has been put into contact with a tissue surface of a human or animal subject. In a second sub-embodiment, the detection surface is placed into electrical communication with the tissue surface that is adjacent to a portion contacted by the first surface of the delivery system. In yet a third sub-embodiment, the detection surface is placed into electrical communication with both the second surface and the tissue surface. In the first sub-embodiment, a thin layer of electrically conductive material is placed on the detection surface to form a sandwich with the second surface of the drug delivery system. Optionally, a septum between the two electrodes mitigates any tendency of the electrically conductive material to short circuit the path between the two electrodes. The bioelectric module repeatedly monitors the resistance over a path that includes the set of electrodes and material in the second surface or the tissue surface or material in both the second surface and the tissue surface, to determine if the resistance is within a predetermined limit. The parameters associated with the electrically conductive material and the bioelectric module are configured so the resistance provides a good measure of the state of coupling to the drug delivery system.

Although in this first detection modality, the two conducting electrodes are placed in electrical communication with a surface, they need not be placed directly on the surface. In a related embodiment, the electrodes are separated from the surface by a dielectric, and properties of this dielectric are utilized in a manner explained later in this description.

The second detection modality of this embodiment, that of detection when the drug delivery system is operatively coupled to the tissue, is carried out using a second set of electrodes, or alternatively, the same set of electrodes, to determine if a quantity related to a RC time constant involving the resistance R and capacitance C, experienced over a path that includes the set of electrodes and material in the second surface or the tissue surface or material in both the second surface and the tissue surface, is within a predetermined limit. Skin proximity (even without direct electrical contact) modifies the effective or apparent capacitance between these two electrodes The measurement in this modality is distinct from the measurement made in the first modality. For this measurement operation, a potential difference or current is momentarily applied across the second pair of electrodes. In one sub-embodiment, which assumes R and C are in series, the RC time constant is determined on the basis of monitoring the rate at which charge builds up on the capacitance. Alternatively, in another sub-embodiment, which assumes that R and C are in parallel, the time constant is determined on the basis of monitoring the rate at which the charge decays.

Skin proximity (even without direct electrical contact) modifies the effective or apparent capacitance between these two electrodes. Thus, the relative distance of these two electrodes to the skin will affect the discharge time. Measuring a parameter corresponding to the time constant RC provides a measurement of the proximity of the drug delivery device to the skin. By performing the above measurement sequence repeatedly, it is possible to determine changes in proximity to the skin. Thresholds for the time constant measurement can be established that correspond to a condition in which the patch has made good contact with the skin. In addition, high surface area conductors (such as provided by conductive foam) can be used to increase the magnitude of the capacitance, allowing for a larger range of measurable values. In addition, this method works well without any actual physical contact between the electrode assembly and the skin (i.e., it operates well with the patch substrate or other materials interposing). Optionally, both pairs of electrodes are implemented by a single pair of electrodes or by interlude electrodes.

As discussed above, although the two conducting electrodes are placed in electrical communication with a surface of the bioelectric module, they need not be placed directly on the surface and can be separated from the surface by a dielectric, with the presence of the dielectric modifying the time constant RC. In fact, a judicious selection of measurement parameters is expected to enable operation of the first detection modality—determining proper configuration between the bioelectric module and the drug delivery system—using the same general measurement technique as described in the previous paragraph. In this situation, however, the measurement technique takes advantage of previously determined characteristics of the dielectric to provide a measurement of the sufficiency of the coupling between the bioelectric module and the drug delivery system.

The third detection modality, that of detection when the drug delivery system is already in contact with the tissue, is carried out by circuits that determine if a quantity related to impedance to an AC signal, over a path that includes the set of electrodes and material in the second surface or the tissue surface or material in both the second surface and the tissue surface, is within a predetermined limit. Optionally, other electrical characteristics of the underlying tissue are also determined. The frequency of the AC signal may be selected in ways known in the art, or, alternatively, it may be swept over a known range. Suitable frequencies lie in the range of 1 milliHz to 100 kiloHz. Skin proximity will provide an impedance measurement reflecting a biological tissue, which can then be used to differentiate from other non-biological materials. This modality will also allow for post-processing analysis and further verification of the measured impedance against a database of known and characterized human impedance measurement. The modality can be further refined with machine learning technologies that can further recognize device location in a specific body section or recognize a human signature for a specific patient.

In a related embodiment, the bioelectric module is enhanced with sensors that collect device-specific, environmental or physiological information. In this embodiment, the circuits in the bioelectric module are designed with additional sensors such as accelerometers, gyroscopes, inertial motion units, temperature sensors, heart rate sensors, ECG, EMG, or other chemical, optical, electrical, acoustic, and/or biological sensors. Device-specific or environmental sensors such as accelerometers and temperature sensors would provide information about the operating state of the bioelectric module, and such information can be used as input to refine software programs in the bioelectric module. For instance, accelerometers would collect data that can be used to remove motion artifacts or further validate device proximity to a tissue, and temperature sensors would provide environmental information that can be used to fine-tune battery life or device performance. Physiological sensors would be used to collect information on the subject in order to individualize a drug regimen. As an example, an ECG sensor could provide heart rate information to the control module that could be used to modify drug release.

In a related embodiment, a battery-powered, wirelessly-communicating bioelectric module initiates drug delivery across a device-tissue interface upon close proximity to the skin. In this modality, the bioelectric module triggers release of liquids, chemicals, polymers, lipids, small molecules, macromolecules, peptides, phosphorylated peptides, proteins, glyco proteins, phospho proteins, antibody, antibody fragments, vaccines, DNA, RNA, mRNA, RNAi, vitamins, antigens, inorganic compounds, organic compounds, and any other composition that can be delivered through a biological tissue through controlled, pulsatile or other type of drug delivery mechanism. As an example, the bioelectric module can be integrated to control an iontophoretic drug release setup. Subsequently, the bioelectric module monitors, and maintains suitable therapeutic drug levels in accordance to algorithms stored in its memory module and other data that be received from an information network. The bioelectric module can also be programmed to stop drug release upon a change in device-tissue proximity or upon the completion of a specified drug regimen. Finally, the bioelectric module may contain integrated memory modules for storing and processing information; integrated communication module capable of transmitting data wirelessly to another device or network, including cell phones, computers, tablets, laptops, antennas, radios, health monitoring devices, smart watches, wearable devices other bioelectric devices in close proximity, etc.; integrated communication module for uploading, accessing and downloading cloud storage data; integrated signal processing module for filtering and smoothing sensory information; and integrated security modules that can securely store artifacts used to authenticate the bioelectric device, either by password, certificate or encryption keys.

In a related embodiment, the bioelectric module can detect whether the drug delivery system has been altered in any way after manufacturing. This is accomplished by continuously sampling at a pre-determined rate, such as once every second, the proximity of the module to the patch and the patch to the tissue and determining whether the proximity or contact values are within normal range. In addition, conductive or dielectric features (strips, shapes, thin or thick films) can be placed directly on the drug delivery system substrate, so that additional information about the drug delivery system or its condition can be determined by the control module, such as drug ID, drug manufacturing information, rotational configuration, proper mounting, and the state of the formulation or compound in the drug delivery system, etc., Barcodes or QRS codes could be added to provide additional information on the drugs. This information would allow the bioelectric module to detect and store the drug type, drug delivery device type, device ID, and drug amount, in addition to authenticating that the drug is an approved drug, that is not past its authorized expiration date and not a counterfeit product.

In a related embodiment, the bioelectric module analyzes whether a subject is compliant with a specific drug therapy. In this embodiment, the bioelectric module is programmed with a specific regimen for a drug therapy and the module collects proximity information about a subject once the module has detected that the therapy has started for the first time. In this embodiment, upon application of the bioelectric module to the skin, the bioelectric module stores a timestamp (date and time) of a drug event and subsequently monitors the duration and dosing of drug delivery. When the drug bioelectric module detects a change in proximity value, the module calculates whether the change corresponds to a successful drug administration or a failed drug administration. A corresponding set of measurement values are stored in the bioelectric module memory until the device transmits the information over a secured network to a cloud data storage system. The server of the cloud storage system or alternatively the bioelectric module uses mathematical models to determine drug administration frequency and usage patterns, and the extent to which such patterns comply with a stored protocol. The resulting information is then made available through a web interface or mobile app to the subject and to health care providers.

In a related embodiment, a wirelessly connected bioelectric module would pair with a mobile device to transmit information about the operational status of the device, proximity values of the module to a tissue, and physiological parameters and drug delivery data collected upon drug administration. The bioelectric module may contain an integrated security module that securely stores artifacts used to authenticate the bioelectric device, either by password, certificate or encryption keys and may contain one or more trusted platform modules (TPMs) or secured cryptoprocessors. Upon authentication and proper pairing, the bioelectric module transmits these data sets in a secure fashion to a secure network or mobile device, which then makes available the data to the subject or to health care providers. The user interface of the app would display the drug information, as well as the status of the bioelectric module (on or off) and other pharmaceutical and health information. In addition, compliance and adherence information can be also provided to the user.

In various embodiments, the module has is configured for:

(1) storing a bioelectric module initial system configuration;

(2) storing the initial proximity value, device configuration and electrical properties of a coupled drug delivery system;

(3) processing and comparing temporal changes in proximity, device configuration and electrical values of the drug delivery system, so as to determine if the drug delivery system has been removed, modified or altered in any way;

(4) placing conductive or dielectric features directly on the drug delivery system substrate to provide additional information about the drug delivery system such as drug ID, drug manufacturing information, drug safety data, state of mounting of the drug delivery device, state of the formulation, etc.;

(5) correctly recognizing the type of drug delivery device or drug by verifying the properties of the drug delivery device and/or reading additional information elements such as barcodes or QR coders, in order to warn the subject if the drug is counterfeited or expired;

(6) securely storing and transmitting information, artifacts and data to mobile devices, wearable devices or data networks;

(7) storing artifacts used to authenticate the bioelectric module, either by password, secure certificates or encryption keys;

(8) authenticating and securing the device using cryptoprocessors and trusted platform modules;

(9) executing processes employing signature detection algorithms for compliance to a given therapy so as to determine when a user has started a therapy, when the therapy has ended and whether the time and frequency of application corresponds to the pre-determined frequency of administration and dosing schedule;

(10) enabling the bioelectric device to read the drug type, drug amount and to authenticate that the drug is an approved drug, that is not past its authorized expiration date and not a counterfeit product; and

(11) personalizing drug therapy depending on compliance and adherence measurements of a therapy using on-demand active delivery of molecules.

What is claimed is:

1. An intelligent bioelectric module for use with a drug delivery system, the drug delivery system having first and second surface regions, wherein the first surface region is configured for contact with a tissue surface of a human or animal subject, the module comprising:
    a case;
    a set of at least two electrodes in electrical communication with a detection surface of the case, wherein a set of dielectric materials is disposed between the detection surface and the electrodes;
    wherein the case is configured so that, in use, the detection surface comes into electrical communication with a member selected from the group consisting of (i) the second surface region of the drug delivery system, (ii) the tissue surface that is adjacent to a portion contacted by the first surface region of the drug delivery system, and (iii) combinations thereof; and
    electronics disposed within the case that determines if a quantity related to impedance to an AC signal is within a predetermined limit, wherein the impedance to the AC signal is experienced over a path that includes (a) the set of electrodes and (b) material in a location selected from the group consisting of the second surface region, the tissue surface, and combinations thereof;
    wherein, if the impedance to the AC signal is determined to be within the predetermined limit, the drug delivery system is determined to be coupled to tissue as opposed to non-living material.

2. A module according to claim 1, wherein the electronics repeatedly determines if the quantity is within the predetermined limit, so as to determine over time if the drug delivery system is coupled to tissue as opposed to non-living material.

3. A module according to claim 1, further comprising a layer of electrically conductive material disposed between the detection surface of the module and the second surface region of the drug delivery system.

4. A module according to claim 1, further comprising a septum disposed between the two electrodes to reduce a risk of a short circuit between the electrodes.

* * * * *